(12) United States Patent
Taguchi

(10) Patent No.: US 8,088,836 B2
(45) Date of Patent: Jan. 3, 2012

(54) OXIME ESTER COMPOUNDS AND PHOTOSENSITIVE RESIN COMPOSITIONS USING THE SAME

(75) Inventor: Yuji Taguchi, Wakayama (JP)

(73) Assignee: Nippon Chemical Works Co., Ltd., Wakayama (JP)

( * ) Notice: Subject to any disclaimer, the term of this patent is extended or adjusted under 35 U.S.C. 154(b) by 164 days.

(21) Appl. No.: 12/656,769

(22) Filed: Feb. 16, 2010

(65) Prior Publication Data

US 2010/0210749 A1 Aug. 19, 2010

(30) Foreign Application Priority Data

Feb. 16, 2009 (JP) ................... 2009-032111

(51) Int. Cl.
*C08F 2/50* (2006.01)
*C08G 18/83* (2006.01)
*C07D 209/82* (2006.01)

(52) U.S. Cl. .............. 522/34; 522/50; 522/63; 548/441; 548/444

(58) Field of Classification Search .................... 522/34, 522/50, 63; 548/441, 444
See application file for complete search history.

(56) References Cited

U.S. PATENT DOCUMENTS

| | | | |
|---|---|---|---|
| 3,558,309 | A | 1/1971 | Laridon et al. |
| 4,202,697 | A | 5/1980 | Van Goethem et al. |
| 4,255,513 | A | 3/1981 | Laridon et al. |
| 4,590,145 | A | 5/1986 | Itoh et al. |
| 2001/0012596 | A1 * | 8/2001 | Kunimoto et al. ............ 430/138 |

FOREIGN PATENT DOCUMENTS

| | | |
|---|---|---|
| JP | 2000-80068 | 3/2000 |
| JP | 2001-233842 | 8/2001 |
| JP | 2006-516246 | 6/2006 |
| WO | 2008/078678 | 7/2008 |

OTHER PUBLICATIONS

Machine English translation of JP 2006-016545; Kamimura et al.; pub. Jan. 19, 2006.*

* cited by examiner

*Primary Examiner* — Mark Eashoo
*Assistant Examiner* — Jessica Paul
(74) *Attorney, Agent, or Firm* — Wenderoth, Lind & Ponack, L.L.P.

(57) ABSTRACT

An oxime ester compound represented by the following general formula (I):

[Chemical Formula 1]

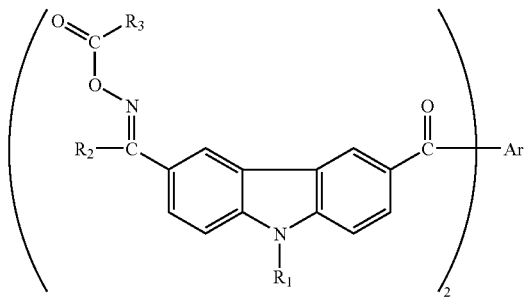

(the symbols of which are defined in the specification) is used as the photopolymerization initiator in a photosensitive resin composition.

3 Claims, No Drawings

OXIME ESTER COMPOUNDS AND PHOTOSENSITIVE RESIN COMPOSITIONS USING THE SAME

TECHNICAL FIELD

The present invention relates to novel oxime ester compounds, to photopolymerization initiators using the same, and to photosensitive resin compositions comprising the compounds as photopolymerization initiators.

BACKGROUND ART

Photosensitive resin compositions are composed mainly of a polymerizable compound with an ethylenic unsaturated bond, and a photopolymerization initiator, and the ethylenic unsaturated compound is usually one that can be cured by ultraviolet irradiation.

Polymerization curing requires a suitable photopolymerization initiator, with ultraviolet irradiation resulting in production of active radicals by the photopolymerization initiator, which reacts with the ethylenic unsaturated compound for polymerization.

The light source used to obtain fine lines by polymerization is usually light of 365 nm or 405 nm. In addition, since photosensitive resin compositions with sensitivity to short wavelength light sources allow fine printing, photopolymerization initiators with excellent sensitivity for 365 nm or 405 nm light sources are desired.

Such photosensitive resin compositions with sensitivity to short wavelength light sources are used in various fields including photocuring inks, photosensitive printing plates, dry film resists, color filters and the like.

Patent documents 1-4 mention oxime ester derivatives, and the use of oxime ester derivatives as photopolymerization initiators is known.

Also, Patent documents 5 and 6 describe O-acyloxime photoinitiators with higher sensitivity. However, these O-acyloxime photoinitiators are also unsatisfactory as photopolymerization initiators with 365 nm or 405 nm light sources, and even higher sensitivity is desired.

PRIOR ART DOCUMENTS

Patent Documents

[Patent document 1] U.S. Pat. No. 3,558,309
[Patent document 2] U.S. Pat. No. 4,255,513
[Patent document 3] U.S. Pat. No. 4,590,145
[Patent document 4] U.S. Pat. No. 4,202,697
[Patent document 5] Japanese Unexamined Patent Publication No. 2000-80068
[Patent document 6] Japanese Unexamined Patent Publication No. 2001-233842

SUMMARY OF THE INVENTION

Problems to be Solved by the Invention

Since the conventional oxime ester-based photopolymerization initiators have not had high absorption at 365 nm and 405 nm, and the desired sensitivity has not been satisfactorily obtainable, the invention was developed to solve this problem.

It is therefore an object of the invention to obtain a photopolymerization initiator with greater photoabsorption at 365 nm and 405 nm than the prior art, as well as high sensitivity, and to obtain a photosensitive resin composition comprising the same.

Means for Solving the Problems

The invention achieves this object by providing novel oxime ester compounds represented by the following general formula (I), and photopolymerization initiators comprising the compounds.

The invention relates to an oxime ester compound represented by general formula (I):

[Chemical Formula 1]

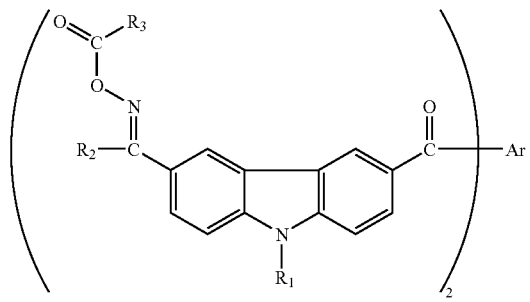

(wherein $R_1$ and $R_2$ each represent methyl or ethyl, $R_3$ represents methyl or phenyl, and Ar represents a bond or phenylene, naphthylene or thienylene), a photopolymerization initiator employing it, and a photosensitive resin composition comprising the foregoing.

Effect of the Invention

Since the oxime ester compounds of the invention have excellent photosensitivity, resolution and stability over time, and particularly the absorbance at 365 nm and 405 nm is higher than hitherto possible, they are useful as photopolymerization initiators with an i-beam light source, or as photosensitive resin compositions.

BEST MODE FOR CARRYING OUT THE INVENTION

The oxime ester compounds of the invention will now be explained in detail by photopolymerization initiators using them and photosensitive resin compositions comprising them.

The compounds represented by general formula (I) above according to the invention are particularly characterized in that $R_1$ and $R_2$ each represent methyl or ethyl, $R_3$ represents methyl or phenyl and Ar represents a bond, phenylene, naphthylene or thienylene.

Particularly preferred among the oxime ester compounds of the invention are those of general formula (I) wherein $R_1$ is ethyl, $R_2$ is methyl, $R_3$ is methyl and Ar is phenylene or thienylene, from the viewpoint of satisfactory photosensitivity, resolution and stability over time.

The following reaction is suitable for obtaining an oxime as the intermediate of the invention.

The synthesis may involve reaction of an aldehyde or ketone and hydroxylamine hydrochloride in a polar solvent such as ethanol in the presence of a base such as sodium acetate or pyridine.

An oxime ester compound of the invention represented by general formula (I) can generally be produced in the following manner.

First, a carbazole-based compound represented by the following general formula (II):

[Chemical Formula 2]

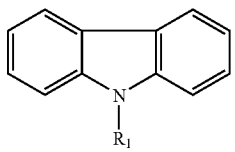

(wherein $R_1$ is methyl or ethyl)
and acid chlorides represented by the following general formula (III):

[Chemical Formula 3]

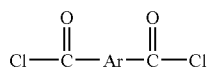

(wherein Ar is a bond or phenylene, naphthylene or thienylene)
and the following general formula (IV):

[Chemical Formula 4]

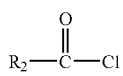

(wherein $R_2$ is methyl or ethyl),
are reacted in the presence of a metallic chloride such as aluminum chloride, to obtain an acyl compound represented by the following general formula (V):

[Chemical Formula 5]

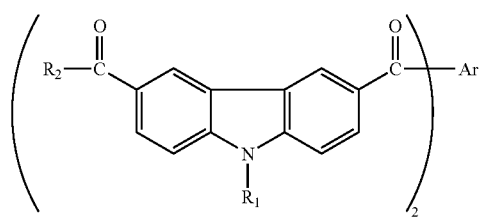

(wherein $R_1$, $R_2$ and Ar have the same definitions as above).

Next, the compound represented by general formula (V) above is reacted in the presence of a base such as hydroxylamine hydrochloride or pyridine to obtain an oxime compound represented by the following general formula (VI):

[Chemical Formula 6]

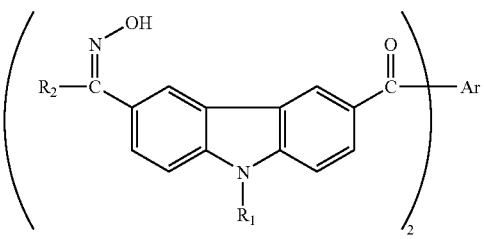

(wherein $R_1$, $R_2$ and Ar have the same definitions as above).

The compound of general formula (VI) is then reacted with an acid chloride represented by the following general formula (VII):

[Chemical Formula 7]

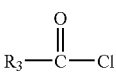

(wherein $R_3$ is methyl or ethyl),
to obtain an oxime ester compound of the invention represented by the following general formula (I):

[Chemical Formula 8]

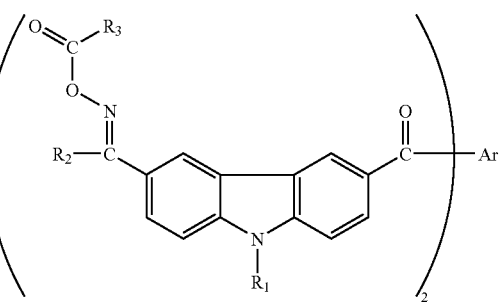

(wherein $R_1$, $R_2$, $R_3$ or Ar have the same definitions as above).

The oxime ester compounds of the invention are useful as photopolymerization initiators for compounds having radical polymerizable ethylenic unsaturated bonds.

A photosensitive resin composition of the invention will now be explained.

The photosensitive resin composition is a component comprising a photopolymerization initiator according to the invention, with an ethylenic unsaturated bond-containing compound, a binder, etc. If necessary, it may be prepared with admixture of additives such as thermal polymerization initiators or plasticizers.

As examples of compounds with ethylenic unsaturated double bonds according to the invention there may be mentioned esters of unsaturated carboxylic acids and unsaturated carboxylic acids with aliphatic polyhydroxy compounds, esters of unsaturated carboxylic acids with aromatic polyhydroxy compounds, and esters obtained by esterification reaction of unsaturated carboxylic acids and polybasic carboxylic acids with polyhydroxy compounds.

As examples of esters of unsaturated carboxylic acids and aliphatic polyhydroxy compounds according to the invention there may be mentioned acrylic acid esters such as ethyleneglycol diacrylate, triethyleneglycol diacrylate, trimethylolethane triacrylate, trimethylolpropane triacrylate, pentaerythritol diacrylate, pentaerythritol triacrylate, pentaerythritol tetraacrylate, dipentaerythritol tetraacrylate, dipentaerythritol pentaacrylate, dipentaerythritol hexaacrylate and glycerol acrylate, methacrylic acid esters such as triethyleneglycol dimethacrylate, trimethylolethane trimethacrylate, trimethylolpropane trimethacrylate, pentaerythritol dimethacrylate, pentaerythritol trimethacrylate, pentaerythritol tetramethacrylate, dipentaerythritol dimethacrylate, dipentaerythritol trimethacrylate and dipentaerythritol tetramethacrylate, and itaconic acid esters, crotonic acid esters or maleic acid esters of aliphatic polyhydroxy compounds.

As examples of esters of unsaturated carboxylic acids and aromatic polyhydroxy compounds according to the invention there may be mentioned hydroquinone diacrylate, hydroquinone dimethacrylate, resorcin diacrylate and resorcin dimethacrylate.

As examples of esters obtained by esterification reaction of unsaturated carboxylic acids and polybasic carboxylic acids with polyhydroxy compounds there may be mentioned acrylic acid-phthalic acid-ethylene glycol condensation products, acrylic acid-maleic acid-diethyleneglycol condensation products, methacrylic acid-terephthalic acid-pentaerythritol condensation products and acrylic acid-adipic acid-butanediol-glycerin condensation products.

As examples of compounds with ethylenic unsaturated double bonds to be used for the invention there may be mentioned acrylamides such as ethylenebisacrylamide, allyl esters such as diallyl phthalate, and vinyl group-containing compounds such as divinyl phthalate. As examples of polymers with ethylenic unsaturated double bonds on the main chain there may be mentioned polyesters obtained by polycondensation reaction of unsaturated divalent carboxylic acids and dihydroxy compounds, and polyamides obtained by polycondensation reaction of unsaturated divalent carboxylic acids and diamines.

As polymers with ethylenic unsaturated double bonds on side chains according to the invention there may be mentioned condensation polymers of dihydroxy or diamine compounds with divalent carboxylic acids having unsaturated bonds on the side chain, such as itaconic acid, propylidenesuccinic acid or ethylidenemalonic acid. Polymers with functional groups such as hydroxy groups or halogenated methyl groups on the side chain, for example, polymers obtained by polymer reaction with polyvinyl alcohols, poly(2-hydroxyethyl methacrylate), epoxy resins, phenoxy resins, polyepichlorohydrin or the like with unsaturated carboxylic acids such as acrylic acid, methacrylic acid or crotonic acid, may also be used.

These binders may be obtained, for example, by radical polymerization of polymerizable monomers. As examples of such monomers there may be mentioned styrene, styrene derivatives such as vinyltoluene, α-methylstyrene, p-methylstyrene and p-ethylstyrene, vinyl alcohol esters such as acrylamide and acrylonitrile, alkyl methacrylate esters such as methyl methacrylate, ethyl methacrylate, propyl methacrylate, butyl methacrylate, pentyl methacrylate and hexyl methacrylate, and maleic acid, maleic anhydride, cinnamic acid, itaconic acid, crotonic acid or the like.

The amount of binder used for the invention is preferably 30-1000 parts by weight and more preferably 50-150 parts by weight with respect to 100 parts by weight of the ethylenic compound.

The oxime ester compound of the invention may be used together with a known photopolymerization initiator such as mentioned below.

As examples of photopolymerization initiators there may be mentioned acetophenone, benzophenone, 4,4'-bis(diethylamino)-benzophenone, 4-(methylphenylthio)-phenylphenylketone, benzyldimethylketal, 2-methyl-1-methylthiophenyl-2-morpholinopropan-1-one, 2-benzyl-2-dimethylamino-1-(4-morpholinophenyl)butan-1-one, p-diethylethyl aminobenzoate, thioxanthone, 2,5-diethylthioxanthone, 2-chloroxanthone, isopropylthioxanthone, 1-chloro-4-propoxy-thioxanthone, 2-(o-chlorophenyl)-4,5-diphenylimidazole dimer, 2-(o-fluorophenyl)-4,5-diphenylimidazole dimer, 2-(o-methoxyphenyl)-4,5-diphenylimidazole dimer, 2-(p-methoxyphenyl)-4,5-diphenylimidazole dimer, 2-(o-chlorophenyl)-4,5-di(o-methoxyphenyl)imidazole dimer, 9-phenylacridine, 9-(p-toluoyl)acridine, 1,7-bis(9,9'-acridinyl)heptane, N-phenylglycine, bis($\eta^5$-cyclopentadienyl)bis[2,6-difluoro-3-(1H-pyrrol-1-yl)phenyl]titanium, 2-ethylanthraquinone, 1-chloroanthraquinone, 2-phenyl-4,6-bis(trichloromethyl)-s-triazine, 2-(4-methoxyphenyl)-4,6-bis(trichloromethyl)-s-triazine, 2-naphthyl-4,6-bis(trichloromethyl)-s-triazine, 2-(4-methoxynaphthyl)-4,6-bis(trichloromethyl)-s-triazine and 2-methyl-4,6-bis(trichloromethyl)-s-triazine.

The photosensitive resin composition of the invention will normally be used as a solution or dispersion of the oxime ester compound and the polymerizable compound with an ethylenic unsaturated bond.

Examples of solvents to be used include liquid compositions comprising acetone, methyl ethyl ketone, methyl isobutyl ketone, methyl amyl ketone, ethyleneglycol monomethyl ether, ethyleneglycol monoethyl ether, ethyleneglycol monopropyl ether, ethyleneglycol monobutyl ether, diethyleneglycol monomethyl ether, diethyleneglycol monoethyl ether, diethyleneglycol monopropyl ether, ethyleneglycol dimethyl ether, ethyleneglycol diethyl ether, diethyl ether, t-butyl methyl ether, t-butyl ethyl ether, hexane, heptane, octane, cyclohexane, benzene, toluene, xylene, methanol, ethanol, isopropanol, 1-butanol, chloroform, N,N'-dimethylformamide or N-methyl-2-pyrrolidone.

The photosensitive resin composition of the invention can be applied for a wide variety of uses including as a printing ink, printing plate, coating material, adhesive, dry film resist, color filter or the like, without any particular restrictions on the purpose of use.

The light source used for exposure according to the invention may be a halogen lamp, xenon lamp, tungsten lamp, metal halide lamp, ultra-high-pressure mercury lamp, high-pressure mercury lamp, medium-pressure mercury lamp, low-pressure mercury lamp, light emitting diode, laser diode, $F_2$ excimer laser, KrF excimer laser, ArF excimer laser or the like.

There are no particular restrictions on the amount of photopolymerization initiator added in the photosensitive resin composition of the invention, but an oxime ester compound of the invention will normally be used at 0.1-50 parts by weight, and from the viewpoint of sensitivity and resolution more preferably 1-40 parts by weight, with respect to 100 parts by weight of the polymerizable compound with an ethylenic unsaturated bond.

Examples of using oxime ester compounds of the invention will now be explained, with the understanding that the invention is not limited by these examples.

EXAMPLES

Example 1

Synthesis of Oxime Ester Compound a. Synthesis of Carbazole Derivative (Acyl Compound)

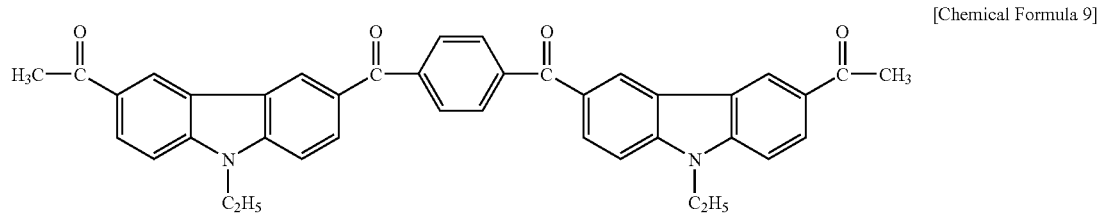

[Chemical Formula 9]

To 5.00 parts of N-ethylcarbazole in 40 ml of $CH_2Cl_2$ there were added 2.73 parts of terephthalic chloride and 3.76 parts of $AlCl_3$. After stirring overnight at room temperature, 2.21 parts of acetyl chloride and 3.76 parts of $AlCl_3$ were added. The reaction mixture was then stirred at room temperature for 4 hours. The reaction mixture was subsequently poured into ice water. The product was extracted with ethyl acetate. The ethyl acetate layer was washed with saturated aqueous $NaHCO_3$ and brine and then dried over anhydrous magnesium sulfate. The solvent was concentrated to obtain 5.91 parts of a light yellow-green solid (76.3%). The solid was used directly without purification for the following reaction.

b. Synthesis of Oxime Compound

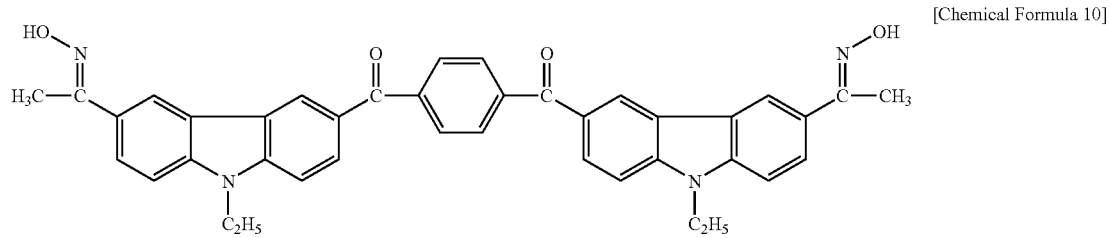

[Chemical Formula 10]

To 3.0 parts of the acyl compound obtained in a. in 30 ml of ethanol there were added 0.76 part of hydroxylammonium chloride and 0.86 part of pyridine. After 10 hours of circulation, the reaction mixture was poured into ice water. The obtained solid was filtered and washed with water, and then dissolved in ethyl acetate. It was dried over anhydrous magnesium sulfate and concentrated to obtain 2.80 parts of a light yellow-white solid (89%). The solid was used directly without purification for the following reaction.

c. Synthesis of Oxime Ester Compound

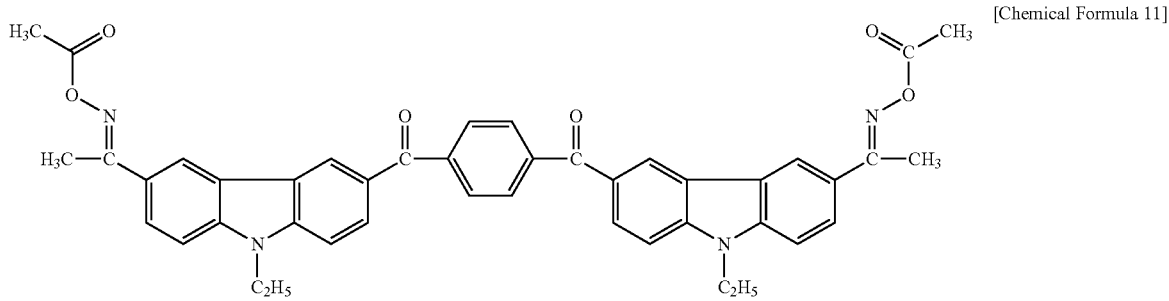

[Chemical Formula 11]

A 1.5 part portion of the oxime compound obtained in b. was dissolved in 25 parts of DMF. After then adding 0.59 part of acetyl chloride to the solution, 0.78 part of triethylamine was added dropwise at 10° C. The mixture was stirred at room temperature for 4 hours, and then the reaction mixture was poured into water and the precipitated solid was filtered. The filtered solid was purified by silica gel column chromatography using $CH_2Cl_2$-hexane (2:1) to obtain 1.05 parts of a light yellow solid (61.8%). The λmax value was 345 nm, and the melting point was 191-202° C.

Examples 2-5

Table 1 shows the specific structures and measurement results for different compounds of the invention represented by the following general formula (IX), which were synthesized by the same method.

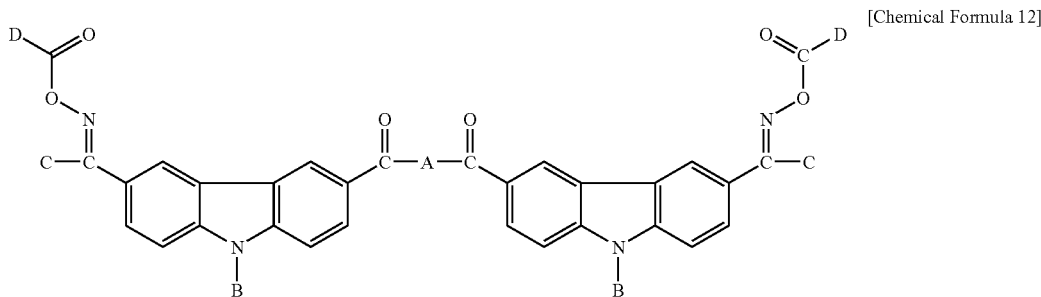

[Chemical Formula 12]

TABLE 1

| Example No. | A | B | C | D | Melting point ° C. | λ max |
|---|---|---|---|---|---|---|
| 2 |  | $C_2H_5$ | $CH_3$ |  | 140-149 | 336 nm |
| 3 | 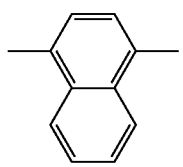 | $C_2H_5$ | $C_2H_5$ | $CH_3$ | 205-218 | 366 nm |
| 4 | 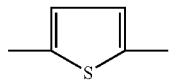 | $C_2H_5$ | $CH_3$ | $CH_3$ | 211-223 | 369 nm |
| 5 | — (Bond) | $CH_3$ | $CH_3$ | $CH_3$ | 133-142 | 336 nm |

Example 6

Production of Photosensitive Resin Composition

The materials listed in Table 2 were combined to obtain a photosensitive resin composition.

TABLE 2

| Material | | Content |
| --- | --- | --- |
| Binder | Toluene and ethylene glycol solution containing methacrylic acid-methyl methacrylate-styrene copolymer (weight ratio: 30-45-25) | 55 parts, solid weight |
| Compound with ethylenic unsaturated double bond | Trimethylolpropane acrylate | 45 parts |
| Photopolymerization initiator | Compounds of Examples 1-5 and Comp. Examples 1 and 2 | 3 parts |

The commercial products shown below were used as photopolymerization initiators for Comparative Examples 1 and 2.

Comparative Example 1

Trade Name: OXE-01 (Ciba Specialty Chemicals, Inc.)

[Chemical Formula 13]

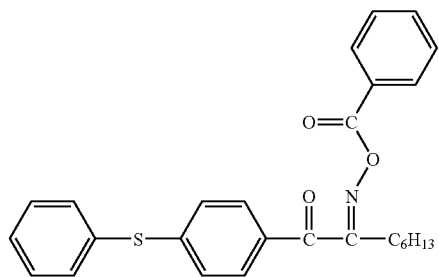

Comparative Example 2

Trade Name: OXE-02 (Ciba Specialty Chemicals, Inc.)

[Chemical Formula 14]

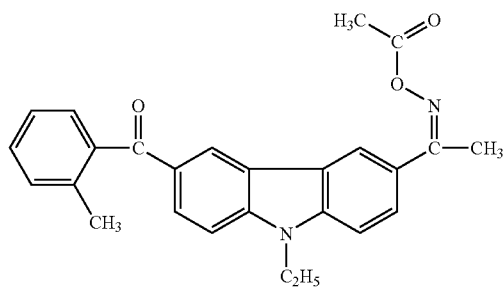

Next, each of the photosensitive resin compositions shown in Table 2 were coated onto a glass panel to a film thickness of 3 μm using a spin coating machine, and were dried in an oven at 80° C. for 3 minutes. An ultrahigh-pressure mercury lamp was used for exposure with different exposure doses. A 1.0 wt % sodium carbonate aqueous solution was then sprayed onto each for 3 minutes at 30° C. to remove the unexposed sections.

Table 3 shows the results for Examples 1-5 and Comparative Examples 1-2.

The sensitivities shown here represent the exposure doses that can form 25 μm resist patterns of the proper dimensions.

A lower exposure dose indicates higher sensitivity in Table 3, and the photosensitive resin compositions of the invention exhibited more excellent sensitivity and resolution than the comparative examples.

TABLE 3

| | Sensitivity (mJ/cm$^2$) |
| --- | --- |
| Example 1 | 82 |
| Example 2 | 86 |
| Example 3 | 77 |
| Example 4 | 75 |
| Example 5 | 83 |
| Comp. Example 1 | 250 |
| Comp. Example 2 | 98 |

INDUSTRIAL APPLICABILITY

The oxime ester compounds of the invention have excellent photoabsorption at 365 nm and 405 nm, compared to prior art products. In addition, a photosensitive resin composition comprising a polymerizable compound with an ethylenic unsaturated bond and an oxime ester compound of the invention as a photopolymerization initiator exhibits excellent photosensitivity in the aforementioned wavelength range, resolution and storage stability.

Since the photopolymerization initiator in the photosensitive resin composition of the invention generates active radicals by ultraviolet irradiation in the wavelength range described above so that the ethylenic unsaturated compound reacts efficiently for polymerization, the composition can be used in a variety of fields including photocuring inks, photosensitive printing plates, dry film resists and color filters.

The invention claimed is:

1. An oxime ester compound represented by the following general formula (I):

Chemical Formula 1

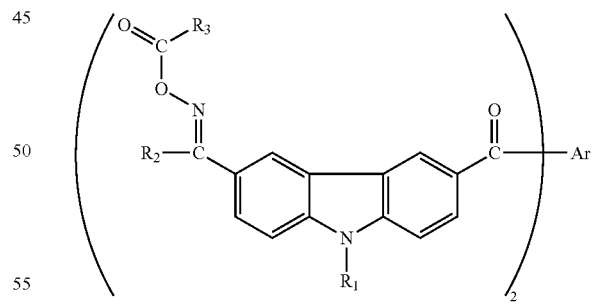

wherein $R_1$ and $R_2$ represent methyl or ethyl, $R_3$ represents methyl or phenyl, and Ar represents a bond or phenylene, naphthylene or thienylene.

2. A photopolymerization initiator comprising an oxime ester compound according to claim 1 as an active ingredient.

3. A photosensitive resin composition obtained by adding a photopolymerization initiator according to claim 2 to an ethylenic unsaturated bond-containing polymerizable compound.

* * * * *